US009629983B2

(12) United States Patent
Sung

(10) Patent No.: US 9,629,983 B2
(45) Date of Patent: Apr. 25, 2017

(54) ALL IN ONE ANTIMICROBIAL DRESSING FOR CATHETER COVERAGE

(71) Applicant: Ethicon, Inc., Somerville, NJ (US)

(72) Inventor: An-Min Jason Sung, Warren, NJ (US)

(73) Assignee: Ethicon, Inc., Somerville, NJ (US)

( * ) Notice: Subject to any disclaimer, the term of this patent is extended or adjusted under 35 U.S.C. 154(b) by 255 days.

(21) Appl. No.: 13/791,501

(22) Filed: Mar. 8, 2013

(65) Prior Publication Data

US 2014/0257242 A1 Sep. 11, 2014

(51) Int. Cl.
*A61M 25/02* (2006.01)
*A61F 13/00* (2006.01)

(52) U.S. Cl.
CPC ....... *A61M 25/02* (2013.01); *A61F 13/00063* (2013.01); *A61F 2013/00412* (2013.01); *A61M 2025/0246* (2013.01); *A61M 2025/0253* (2013.01); *A61M 2025/0273* (2013.01)

(58) Field of Classification Search
CPC .......... A61M 25/02; A61M 2025/0266; A61M 2025/028; A61M 2025/0273; A61M 2025/0246; A61M 2025/0253; A61M 2005/1586; A61M 2025/0213; A61F 13/00063; A61F 13/023; A61F 13/00021; A61F 13/00
USPC ...................... 604/174, 179, 180; 602/54, 56
See application file for complete search history.

(56) References Cited

U.S. PATENT DOCUMENTS

| 3,918,446 A | 11/1975 | Buttaravoli |
| 4,324,237 A | 4/1982 | Buttaravoli |
| 4,915,694 A | 4/1990 | Yamamoto |
| 5,372,589 A * | 12/1994 | Davis ..................... A61M 25/02 604/174 |
| 5,380,294 A | 1/1995 | Persson |
| 5,554,106 A | 9/1996 | Layman Spillar |
| 5,620,419 A | 4/1997 | Lui |
| 5,685,859 A | 11/1997 | Kornerup |
| 5,686,096 A | 11/1997 | Khan |
| 5,833,665 A | 11/1998 | Bootman |
| 5,885,254 A * | 3/1999 | Matyas .................. A61M 25/02 604/174 |
| 5,968,000 A * | 10/1999 | Harrison et al. ................. 602/41 |
| 6,124,521 A | 9/2000 | Roberts |
| 6,273,873 B1 | 8/2001 | Fleischer |
| 6,689,104 B2 | 2/2004 | Bierman |

(Continued)

FOREIGN PATENT DOCUMENTS

WO  WO9300788 A2  1/1993
WO  WO9721459 A1  6/1997

(Continued)

*Primary Examiner* — Nathan R Price
*Assistant Examiner* — Weng Lee

(57) ABSTRACT

We have disclosed dressing devices that combine the functions of coverage of a catheter insertion site, fluid handling capacity for the puncture site of a catheter, and fixation of the catheter. More specifically, we have disclosed dressing devices comprising a base, a pad, and a dressing film, and the devices possess antimicrobial properties. We further disclose a method of making the disclosed dressing devices, a kit comprising the disclosed dressing devices and a catheter fastener means, a method of installing the dressing devices on a patient's skin over an indwelling catheter, and a method of replacing the disclosed dressing devices.

16 Claims, 17 Drawing Sheets

(56) References Cited

U.S. PATENT DOCUMENTS

| | | | |
|---|---|---|---|
| 6,765,122 B1 | 7/2004 | Stout | |
| 6,841,715 B2 | 1/2005 | Roberts | |
| 6,884,920 B2 | 4/2005 | Worthley | |
| 7,025,749 B2 | 4/2006 | Propp | |
| 7,137,968 B1 | 11/2006 | Burrell | |
| 7,232,427 B2 | 6/2007 | Propp | |
| 7,294,751 B2 | 11/2007 | Propp | |
| 7,294,752 B1 | 11/2007 | Propp | |
| 7,648,485 B2 | 1/2010 | Fleischer | |
| 7,723,559 B2 | 5/2010 | Linnane | |
| 2007/0010778 A1 | 1/2007 | Burrell | |
| 2008/0045905 A1 | 2/2008 | Chawki | |
| 2008/0154168 A1* | 6/2008 | Lutri | A61F 13/0246 602/54 |
| 2008/0221526 A1 | 9/2008 | Fleischer | |
| 2010/0198161 A1 | 8/2010 | Propp | |
| 2012/0197204 A1* | 8/2012 | Helm, Jr. | A61M 25/02 604/176 |
| 2013/0165865 A1* | 6/2013 | Kelvered | A61M 25/02 604/180 |
| 2014/0046238 A1* | 2/2014 | Leibowitz | A61F 13/00063 602/48 |

FOREIGN PATENT DOCUMENTS

| | | |
|---|---|---|
| WO | WO9810823 A1 | 3/1998 |
| WO | WO9815312 A1 | 4/1998 |
| WO | WO02094334 A1 | 11/2002 |

\* cited by examiner

Catheter     Prior Art Foam Material

FIG. 4a _PRIOR ART_
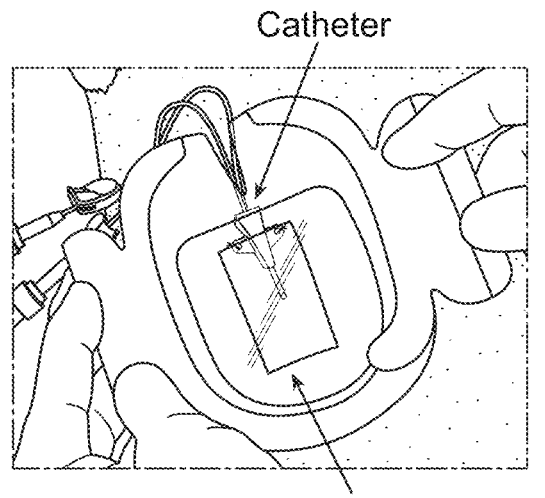
Catheter
Prior Art Dressing with
CHG-Gel Pad
FIG. 4b _PRIOR ART_
Prior Art Dressing with
CHG-Gel Pad
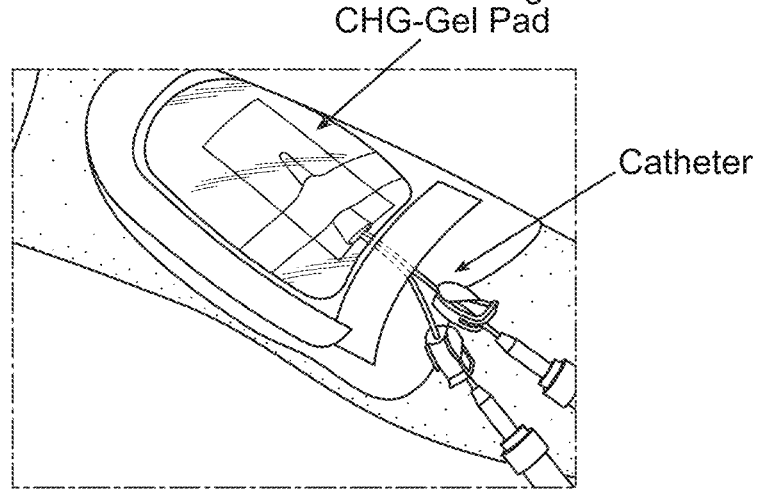
Catheter

FIG. 5 _PRIOR ART_
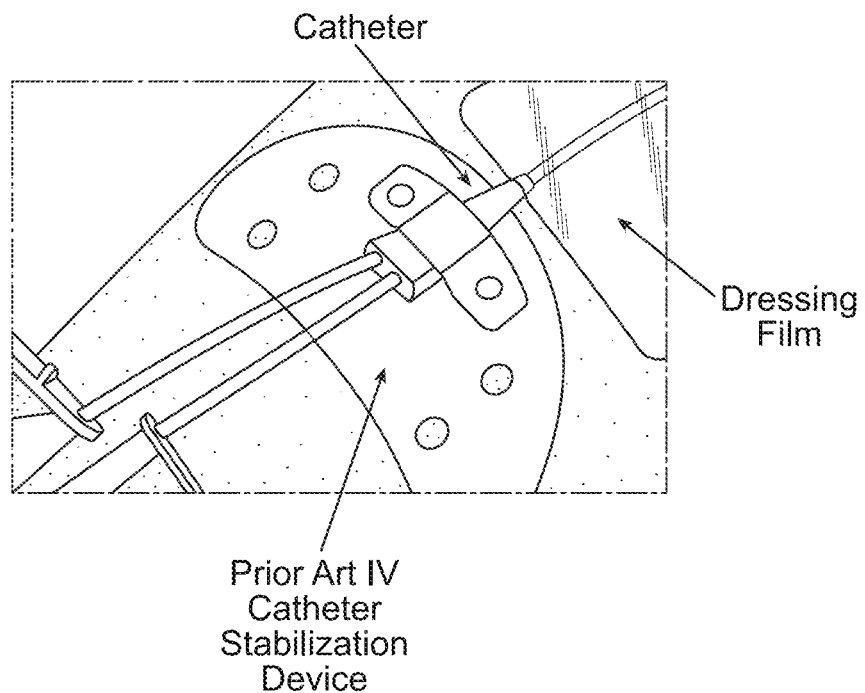

ALL IN ONE ANTIMICROBIAL DRESSING FOR CATHETER COVERAGE

FIELD OF THE INVENTION

The invention relates to devices for the dressing of catheters and to address catheter related bloodstream infections (CRBSIs). In particular, the devices combine the functions of coverage of a catheter insertion site, fluid handling capacity for the puncture site of a catheter, and fixation of the catheter, and they also possess antimicrobial properties.

BACKGROUND OF THE INVENTION

Intravenous (IV) catheters are important to modern medicine, especially to patients under intensive or long term care. Although the catheter provides the necessary vascular access for medications, it places patients at risk for local or systemic infection. Catheter related bloodstream infections (CRBSIs) are potentially lethal for patients and costly to healthcare system. The potential infection can stem from three main sources: 1) skin organisms (skin flora) from either the patient, the healthcare worker, or other patients; 2) a contaminated catheter hub; and/or 3) contaminated infusates (drugs). See FIG. 1 showing the placement of a catheter in a vein and the potential sources of infection.

All sources of infection are potential targets for prevention, and hospitals have implemented measures to prevent CRBSIs. Among the commercially available devices are film dressings that cover a catheter and insertion site, foam materials containing an antimicrobial agent that is used in conjunction with a film dressing, and devices that consist of a combination of a film dressing and antimicrobial material.

While film dressings alone immobilize skin flora and provide a barrier against the surrounding environment, without an antimicrobial agent, the possibility of infection during dressing change remains. See FIG. 2 showing the placement of a prior art film dressing. Many practitioners use a foam material that contains the antimicrobial agent chlorhexidine gluconate (CHG). Johnson & Johnson Corporation markets a commercially available product sold under the trademark BIOPATCH® that is applied around the insertion site of a percutaneous device to prevent localized infection at the insertion site. Such materials provide 360 degree protection, or complete circumferential coverage, but they are non-transparent. Moreover, a film dressing, which typically comes in a separate package from different supplier, is still required to hold the foam material in place and for coverage of the insertion site. See FIG. 3 showing BIOPATCH® and its placement in combination with a separate film dressing.

Transparent film dressings that allow a visual check on a catheter insertion site are advantageous, and it was recognized that a one-step dressing for catheters would be very practical for dressing catheters. 3M Corporation markets a commercially available IV site transparent dressing sold under the trademark TEGADERM™-CHG (clorhexidine gluconate) that is claimed to reduce the incidence of CRBSIs, with the CHG being the antimicrobial agent. The CHG is embedded in a hydrogel pad. The gel pad does not have a slit to go around the device, so it can only be laid on top of the catheter. Thus, the device fails to provide 360 degree or complete circumferential coverage around the insertion site. See FIG. 4 showing TEGADERM™-CHG and its placement over a catheter site.

In addition to the infection concern, other issues such as "pistoning" or "dislodging" of a catheter create problems during dressing change. Separate devices are commonly used to fixate a catheter wing onto the skin of a patient to prevent the pistoning or dislodging problems. C. R. Bard, Inc. markets a commercially available stabilization apparatus sold under the trademark STATLOCK that is sometimes used to fixate a catheter hub to the skin of a patient to prevent a catheter from moving out of position. While it is beneficial when removing a dressing for change, it is not a part of the dressing film, and STATLOCK, see FIG. 5 showing STATLOCK and its placement.

There is a need to provide a device with antimicrobial properties that combines the functions of coverage of a catheter insertion site, fluid handling capacity for the puncture site of a catheter, and fixation of the catheter, and which also possesses antimicrobial properties.

SUMMARY OF THE INVENTION

The invention discloses IV catheter dressing devices that combine the coverage, antimicrobial, and fixation functions together to fight against CRBSIs. In one embodiment, the dressing device has a base connected to a pad and to a dressing film, the base, the pad, and the dressing film each having a proximal surface facing a patient's skin and a distal surface facing away from the skin; the pad has a slit extending from a perimeter of the pad to an aperture proximate to a center of the pad and an antimicrobial agent; the base is connected to the pad by a connector bridging the base and the perimeter of the pad; the dressing film also has an adhesive disposed on the proximal surface of the dressing film and has a first portion and a second portion and the proximal surface of the first portion of the dressing film is adhesively attached to the distal surface of the base; furthermore, the dressing film has a first release paper attached to the proximal surfaces of the first portion of the dressing film and the base and a second release paper attached to the proximal surface of the second portion of the dressing film; and the second portion of the dressing film is folded onto the first portion of the dressing film so that the distal surface of the first portion of the dressing film is in proximity to the distal surface of the second portion of the dressing film.

In another embodiment, a spin is embedded into the dressing film of the dressing device dividing the dressing film into a primary portion and a secondary portion and adapted to split the dressing film into two separate portions upon removal of the spine. Also disclosed is a method of making the dressing device, a method of installing the dressing device on a patient's skin over an indwelling catheter, a kit comprising the dressing device and a catheter fastener means, and a method of replacing the dressing device.

These and other objects of the present invention will be apparent from the following description, appended claims, and from practice of the invention.

BRIEF DESCRIPTION OF THE FIGURES

FIG. 4a illustrates a prior art catheter dressing with a CHG gel pad, similar to TEGADERM™-CHG, and its placement over an IV catheter insertion site.

FIG. 4b illustrates the prior art catheter dressing with a CHG gel pad shown in FIG. 4a after its placement over an IV catheter insertion site.

FIG. 5 illustrates a prior art self-adhesive IV catheter stabilization device, similar to STATLOCK®, and its placement over an IV catheter insertion site.

FIG. 14a illustrates the positioning of the dressing device with a pad in proximity to an indwelling catheter insertion site opposite the tubing of the catheter and the insertion of the catheter into the aperture of the pad through the slit.

FIG. 14b illustrates the removal of the first release paper attached to the proximal surfaces of the first portion of the dressing film and the base.

FIG. 14c illustrates the step of adhesively attaching the proximal surfaces of the first portion of the dressing film and the base to the patient's skin.

FIG. 14d illustrates the removal of the second release paper attached to the proximal surfaces of the second portion of the dressing film and the frame.

FIG. 14e illustrates the step of unfolding and adhesively attaching the proximal surfaces of the second portion of the dressing film and the frame to the patient's skin.

FIG. 14f illustrates the dressing device fully installed over an indwelling catheter on a patient with the removable frame removed from the distal surface of the dressing film.

DETAILED DESCRIPTION OF THE INVENTION

Figure 1:
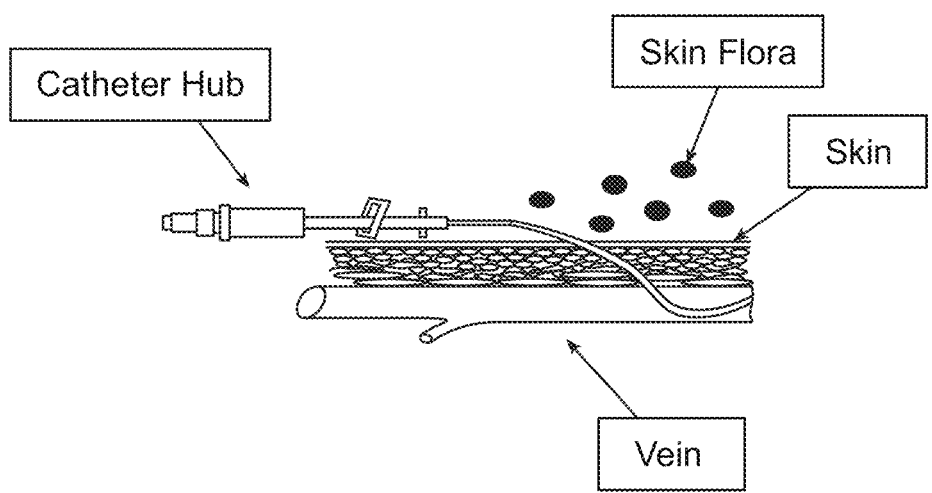
FIG. 1 illustrates the placement of an intravenous catheter in a vein and the potential sources of infection.
Figure 2:
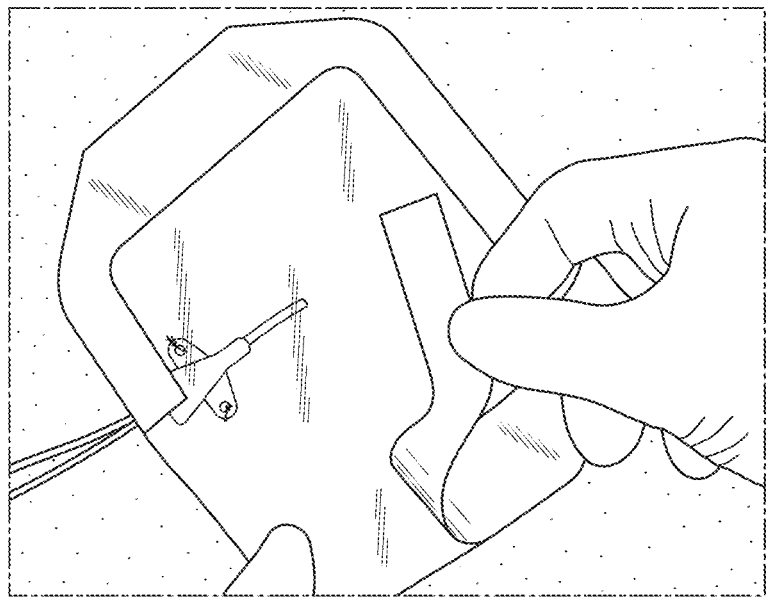
FIG. 2 illustrates the placement of a prior art film dressing over an IV catheter insertion site.
Figure 3A:
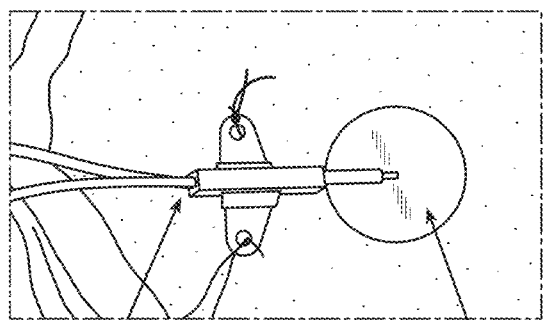
FIG. 3a illustrates a prior art foam material, such as BIOPATCH®, that contains the antimicrobial agent CHG, and its placement around the insertion site of an IV catheter
Figure 3B:
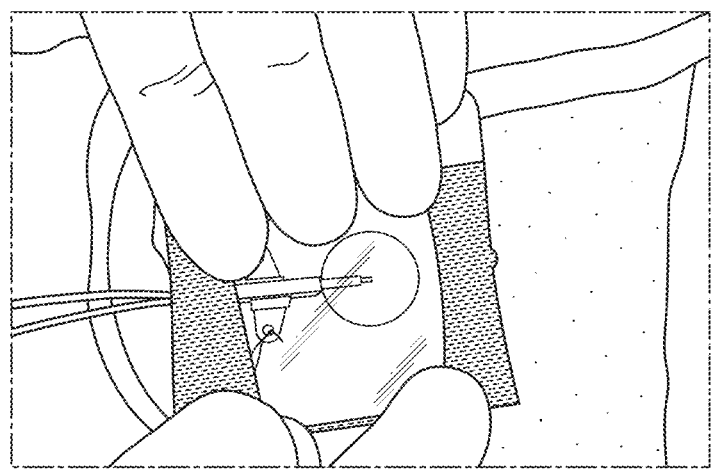
FIG. 3b illustrates the prior art foam material shown in FIG. 3a in combination with a separate film dressing.

An objective of this disclosure is to provide solutions to address CRBSIs. All sources of CRBSIs are potential targets for prevention, but the focus for this invention concerns infection from skin flora. Particularly, the invention discloses IV catheter dressing devices that combine the coverage, antimicrobial, and fixation functions together to fight against CRBSIs. The integration of these multiple features reduces the steps of the dressing procedure for practitioners and the inventory items for the hospital.

This disclosure describes dressing devices designed with absorptive materials capable of fluid absorption that prevent the accumulation of fluid at and around a catheter insertion site by wicking the fluid away from the skin of a patient to reduce the occurrence of skin maceration and infection. Removal of fluid is known to reduce skin maceration, and the fluid is transported away from skin by the wicking mechanism and absorption mechanism. The dressing devices disclosed herein also comprise antimicrobial agents incorporated into at least partially transparent materials that intimately surround a catheter insertion site providing complete 360 degree antimicrobial protection to the insertion site while allowing for visibility of the catheter and insertion site.

An embodiment comprising an integrated fixation means is also disclosed. Particularly, the fixation means is non-adhesive, thus making application and removal of the dressing device easier than with dressing devices that comprise fixation means consisting of an adhesive.

Additional features that make dressing device removal easy are also disclosed. Specifically, the invention discloses an embodiment wherein there is non-adhesive film or layer above the insertion site of the catheter. In another embodiment, the dressing device comprises a two section design that separates the fixation portion of the device from the antimicrobial and coverage portion of the device with a spine for easy tear away. These features make dressing removal/change easier than with prior art dressing devices and also assist with avoiding dislodgement of a catheter during a dressing change.

It is to be understood that the figures discussed in the following description are for illustrative purposes only to show the relationship of the elements of the dressing device and not necessarily drawn to scale.

As described herein, dressing devices 10 disclosed can be made by providing a base 20 connected to a pad 30 by a connector 70 bridging the base 20 and the perimeter of the pad 30. The pad 30 has an antimicrobial agent and a slit 50 extending from the perimeter of the pad 30 to an aperture 60 proximate to a center of the pad 30. See FIGS. 7a and 7b. The base 20 and the pad 30 each have a proximal surface facing a patient's skin and a distal surface facing away from the skin. A dressing film 40 with a proximal surface facing the patient's skin and a distal surface facing away from the patient's skin and comprising an adhesive 80 disposed on the proximal surface of the dressing film 40 is also provided. The dressing film 40 further has a first portion 90 and a second portion 100. The proximal surface of the dressing film 40 is adhesively attached to the distal surface of the base 20. First 110 and second 120 release papers are attached to the proximal surfaces of first 90 and second 100 portions of the dressing film 40, respectively. Finally, the first portion 90 of the dressing film 40 is folded onto the second portion 100 of the dressing film 40 so that the distal surface of the first portion 90 of the dressing film 40 is in proximity to the distal surface of the second portion 100 of the dressing film 40. See FIGS. 6a-b and 8a-b.

Figure 6A:
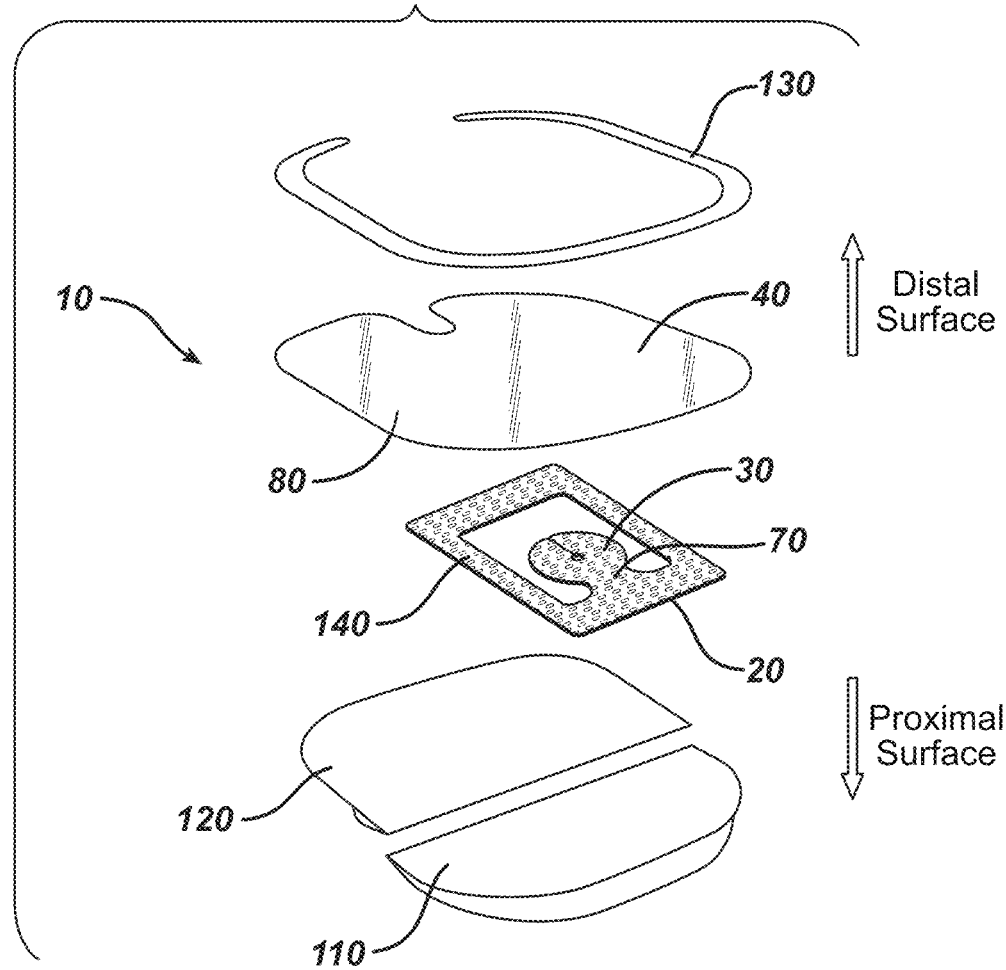
FIG. 6a illustrates an exploded view of a dressing device of the invention comprising a frame comprising an opening connected to a base connected to a pad and to a dressing film comprising first and second release papers.
Figure 6B:
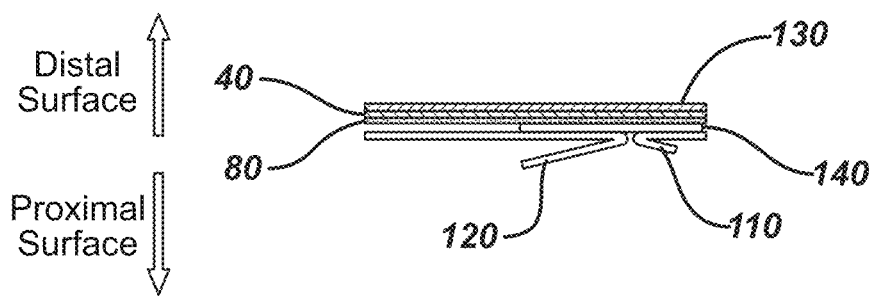
FIG. 6b illustrates a side view of a dressing device of the invention comprising a dressing film with adhesive disposed on the proximal surface of the dressing film, a removable frame attached to a peripheral area of the distal surface of the dressing film, and first and second release papers attached to the proximal surface of the dressing film.

Referring now to FIGS. 6a and 6b, illustrated is an embodiment of a multi-functional dressing device 10 that combines the functions of antimicrobial properties and coverage. The dressing device 10 in FIGS. 6a and 6b provides 360 degree protection around an insertion site of a catheter with translucent or transparent antimicrobial agent impregnated materials that provide visibility to the insertion site.

Referring to FIG. 6a, illustrated is an exploded view of a dressing device 10 of the invention comprising a base 20 connected to a pad 30 by a connector 70 and to a dressing film 40. The base 20, connector 70, pad 30, and dressing film 40 each have a proximal surface facing a patient's skin and a distal surface facing away from the skin. The dressing film 40 may include an adhesive 80 disposed on the proximal surface of the dressing film 40. The dressing film 40 further comprises a first release paper 110 attached to the proximal surfaces of the first portion 90 (not shown in FIG. 6a) of the dressing film 40 and the base 20. The dressing film 40 also has a second release paper 120 attached to the proximal surface of the second portion 100 (not shown in FIG. 6a) of the dressing film 40. The first 110 and second 120 release papers cover and protect the adhesive 80 before application of the dressing device 10 on a patient. The dressing device 10 further comprises a frame 140 connected to the base 20 and comprising an opening 190 (see FIG. 9b, area enclosed by the black line) that surrounds the pad 30 and the connector 70. The frame 140 is adapted to immobilize an indwelling catheter. The frame 140 has a proximal surface facing a patient's skin and a distal surface facing away from the skin.

The pad 30 has an antimicrobial agent and a slit 50 (not shown in FIG. 6a; see FIGS. 7a-c) extending from a perimeter of the pad 30 to an aperture 60 (not shown in FIG. 6a; see FIGS. 7a-c) proximate to a center of the pad 30. The base 20 is connected to the pad 30 by a connector 70 bridging the base 20 and the perimeter of the pad 30. The base 20, the pad 30, and the connector 70 comprise an antimicrobial agent. The dressing film 40 can have a removable frame 130 attached to a peripheral area of the distal surface of the dressing film 40. The removable frame 130 provides rigidity to the dressing device 10 during application of the same on a patient.

FIG. 6b is a side view of a dressing device 10 comprising a dressing film 40 with adhesive 80 disposed on the proximal surface of the dressing film 40 and a removable frame 130 attached to a peripheral area of the distal surface of the dressing film 40. The embodiment shown in FIG. 6b further comprises a frame 140 connected to the base 20 (not shown in FIG. 6b) and comprising an opening 190 (see FIG. 9b, area enclosed by the black line) that surrounds the pad 30 (not shown in FIG. 6b) and the connector 70 (also not shown in FIG. 6b). The dressing film 40 shown in FIG. 6b further comprises a first release paper 110 attached to the proximal surfaces of the first portion 90 (not shown in FIG. 6b) of the dressing film 40 and the base 20 (not shown in FIG. 6b). The dressing film 40 also has a second release paper 120 attached to the proximal surface of the second portion 100 (not shown in FIG. 6b) of the dressing film 40.

Figure 7A:
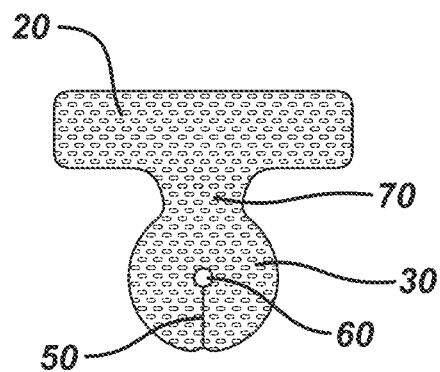
FIG. 7a illustrates a pad of a dressing device having a circular shape.
Figure 7B:
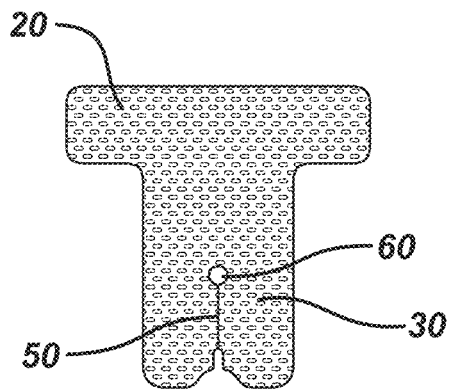
FIG. 7b illustrates a pad of a dressing device having a rectangular shape.
Figure 7C:
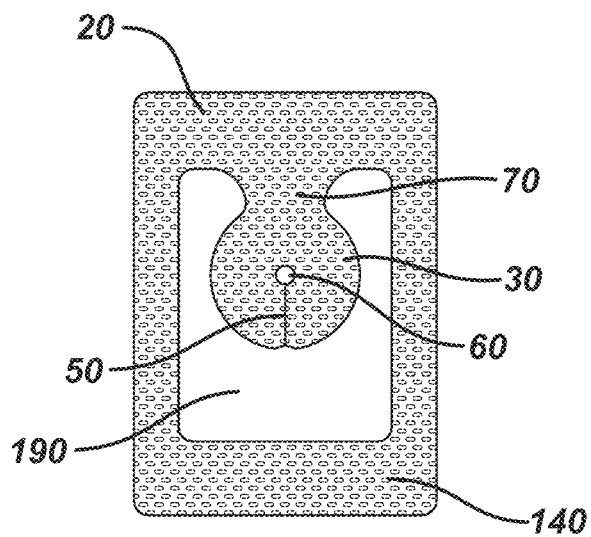
FIG. 7c illustrates a pad of a dressing device having a circular shape and located within the opening of a frame connected to a base.

The pad 30 of the dressing device 10 may be of any suitable shape as shown in FIGS. 7a to 7c. FIG. 7a illustrates a pad 30 of a dressing device 10 having a circular shape, and FIG. 7b illustrates a pad 30 of a dressing device 10 having a rectangular shape. Other suitable shapes include, but are not limited to oval, trapezoidal, or any polygonal shape, with the design adapted such that there is circumferential coverage around the insertion site of an indwelling catheter.

FIG. 7c further illustrates an embodiment of a dressing device 10 comprising a frame 140 connected to a base 20 connected to pad 30 (having a circular shape) through connector 70. The embodiment shown in FIG. 7c reinforces the fixation of a catheter hub to the skin of a patient with the dressing film. The frame 140 is adapted to immobilize an indwelling catheter. The frame 140 has a proximal surface facing a patient's skin and a distal surface facing away from the skin.

Figure 8A:
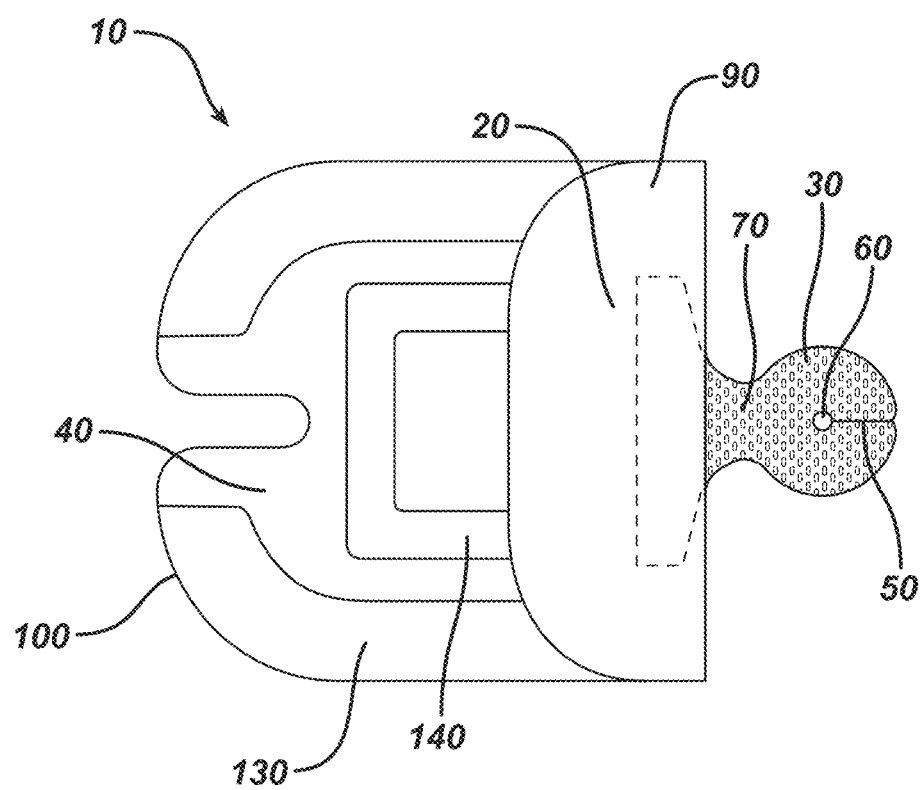
FIG. 8a illustrates the top view (distal surface) of dressing device in the folded state further comprising a frame connected to the base and comprising an opening that surrounds the pad and the connector and showing how the first portion of the dressing film of the device is folded onto the second portion of the dressing film so that the distal surface of the first portion of the dressing film is in proximity to the distal surface of the second portion of the dressing film.

Referring to FIG. 8a, which illustrates the top view of dressing device 10 in the folded state, the embodiment comprises a frame 140 connected to the base 20 (shown by a dotted line) and comprising an opening 190 (see FIG. 10b, area enclosed by the black line) that surrounds the pad 30 and the connector 70. The dressing film 40 comprises an adhesive 80 disposed on the proximal surface of the dressing film 40, and the dressing film 40 is divided into a first portion 90 and a second portion 100, each portion having a releasable liner/paper attached thereto. The first portion 90 of the dressing film can have a size adapted to cover the base 20, and the proximal surface of the first portion 90 of the dressing film 40 is adhesively attached to the distal surface of the base 20. The dressing film 40 further comprises a first release paper 110 (see FIG. 8b) attached to the proximal surfaces of the first portion 90 of the dressing film 40 and the base 20.

Figure 8B:
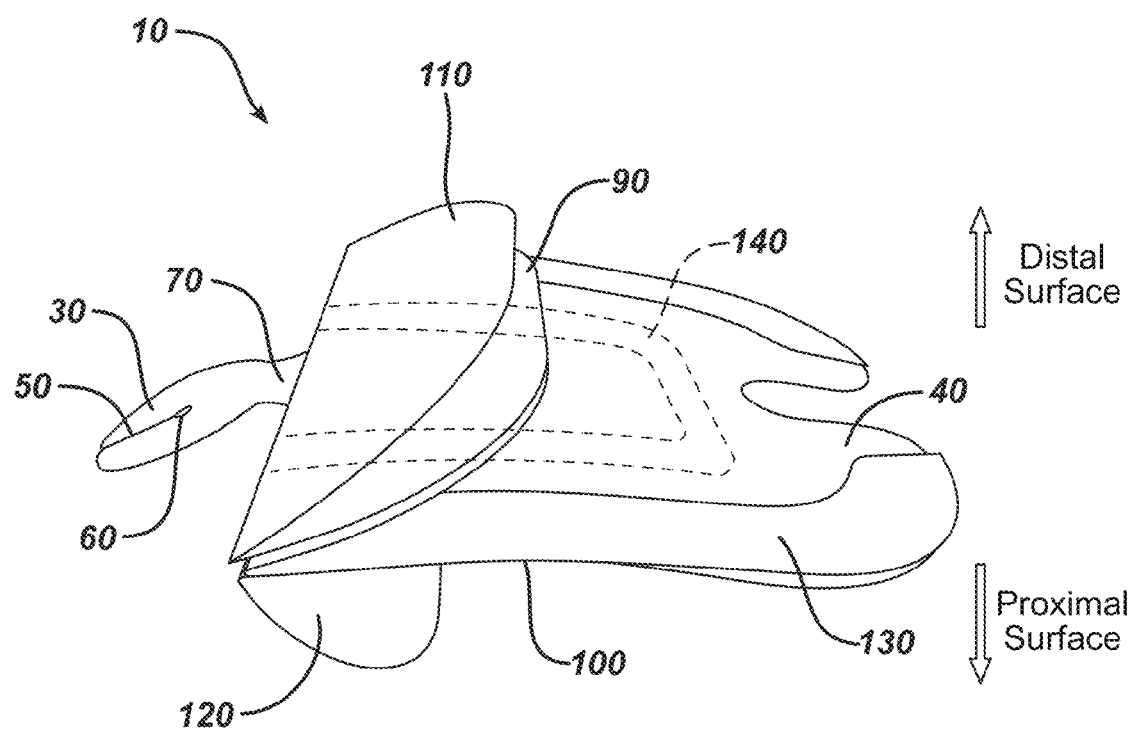
FIG. 8b illustrates the oblique view of the dressing device shown in FIG. 8a in the folded state.

The second portion 100 of the dressing film 40 is proximate to and has a size adapted to cover the connector 70, the pad 30, and the frame 140. The proximal surface of the second portion 100 of the dressing film 40 is adhesively attached to the distal surface of the frame 140. The pad 30 and connector 70 need not be attached to the adhesive 80 as shown in FIGS. 8a and 8b. The dressing film 40 also has a second release paper 120 (see FIG. 8b) attached to the proximal surface of the second portion 100 of the dressing film 40. The first 110 and second 120 release papers cover and protect the adhesive 80 before application of the dressing device 10 on a patient.

FIG. 8a further depicts how the first portion 90 of the dressing film 40 of the device 10 is folded onto the second portion 100 of the dressing film 40 so that the distal surface of the first portion 90 of the dressing film 40 is in proximity to the distal surface of the second portion 100 of the dressing film 40. FIG. 8b, illustrating an oblique view of the dressing device 10 shown in FIG. 8a in a folded state, shows that when the dressing device 10 has a frame 140, the proximal surface of the second portion 100 of the dressing film 40 is adhesively attached to the distal surface of the frame 140 (shown by a dotted line in FIG. 8b to illustrate the frame 140 above the second release paper 120). Accordingly, in this embodiment, the second release paper 120 of the dressing film may be attached to the proximal surfaces of the second portion 100 of the dressing film 40 and the frame 140.

As shown in FIGS. 8a and 8b, the dressing film 40 can have a removable frame 130 attached to a peripheral area of the distal surface of the dressing film 40. The removable frame 130 provides rigidity to the dressing device 10 during application of the same on a patient.

Figure 9A:
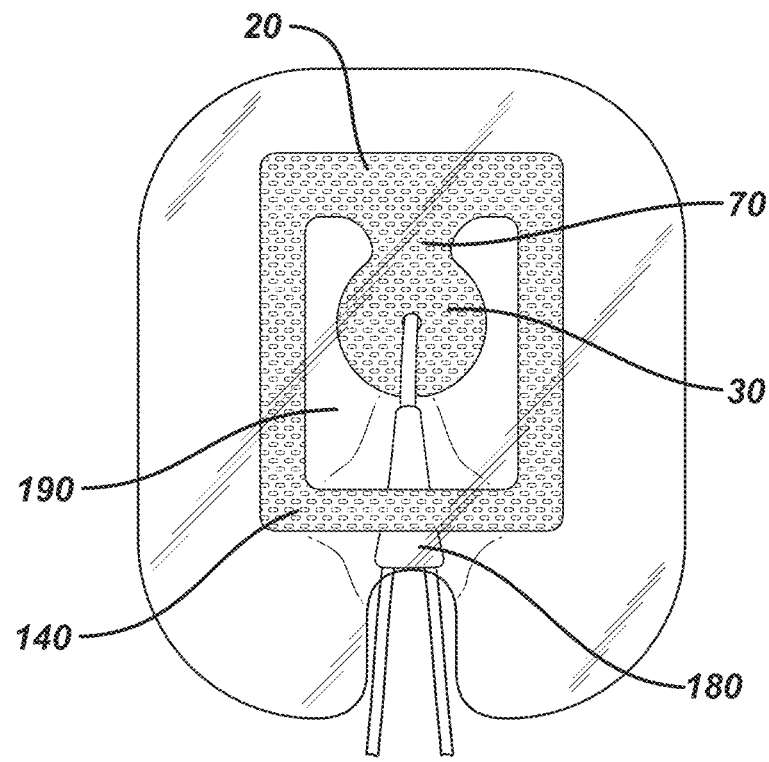
FIG. 9a illustrates the dressing device dressing an indwelling catheter, the dressing device comprising a frame connected to the base and comprising an opening that surrounds the pad and the connector.
Figure 9B:
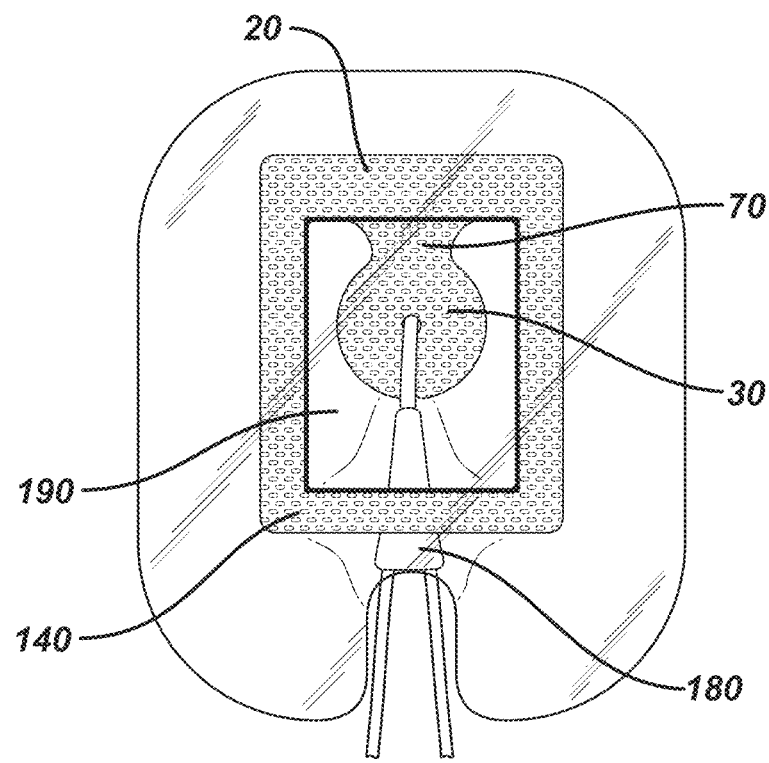
FIG. 9b illustrates how an area of the dressing film in FIG. 9a enclosed by the black line that encompasses the frame opening can be devoid of adhesive to make the removal of the dressing device during dressing change easy.

FIG. 9a illustrates the dressing device 10 depicted in FIGS. 8a and 8b installed over an indwelling catheter 180 in a patient, the dressing device 10 comprising a frame 140 connected to the base 20 and comprising an opening 190 (frame opening) that surrounds the pad 30 that is connected to the base 20 by a connector 70. A dressing film 40, with adhesive 80 disposed on the proximal surface of the dressing film 40, is adhesively attached to the distal surfaces of the frame 140, base, 20, pad 30, and connector 70 when applied over an indwelling catheter 180.

In one embodiment, the second portion 100 of the dressing film 40 may have no adhesive 80 in an area proximate to the distal surface of the pad 30, i.e., the second portion 100 of the dressing film 40 has no adhesive 80 in an area of the pad 30 and immediately surrounding the pad 30. For instance, an area of the dressing film in FIG. 9a enclosed by the black line in FIG. 9b that encompasses the frame opening 190 can be devoid of adhesive 80 to make the removal of the dressing device 10 during dressing change easy. Specifically, the area immediately surrounding the catheter 180 within the frame defined by a black line in FIG. 9b, also defined as frame opening 190, can be optionally devoid of any adhesive 80, while pad 30, base 20, connector 70, and frame 140 contain no adhesive for easy removal of the dressing. This makes removal/changing of the dressing device 10 easier than with prior art dressing devices.

Figure 10:
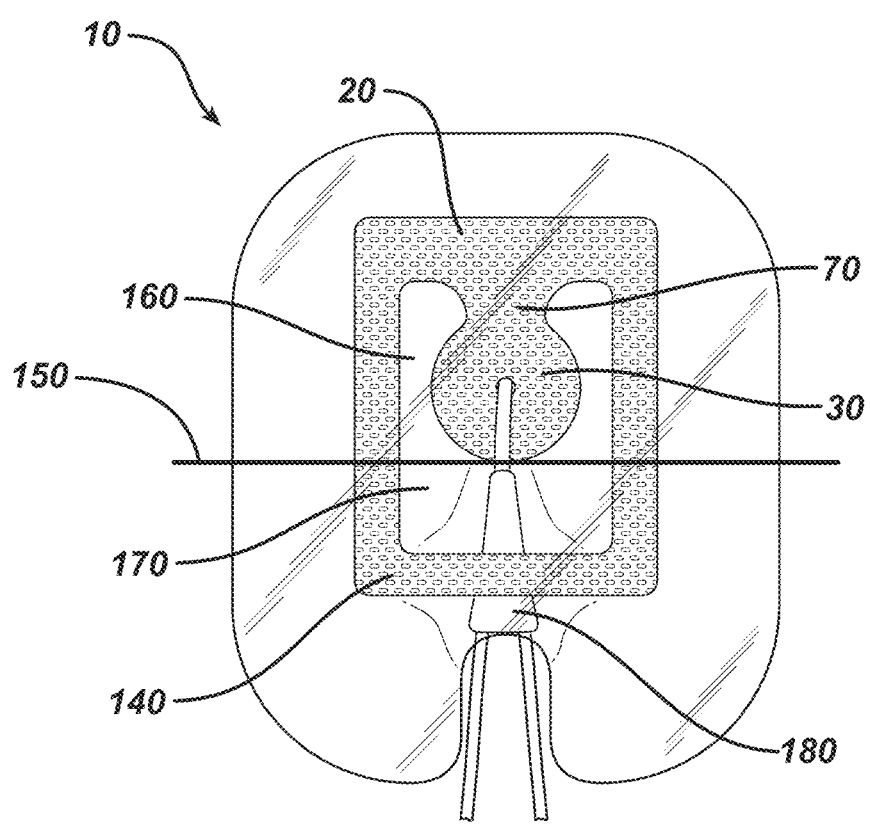
FIG. 10 illustrates a spine embedded into the dressing film dividing the dressing film into a primary portion and a secondary portion.

In another embodiment, a spine 150 is embedded into the dressing film 40 of the dressing device 10 shown in FIGS. 8a-b and 9a-b. As shown in FIG. 10, a spine 150 is embedded into the dressing film 40 dividing the dressing film 40 into a primary portion 160 and a secondary portion 170, the primary portion 160 comprising the base 20, the connector 70, and the pad 30, the secondary portion 170 comprising the portion of the dressing film 40 that would cover at least a part of an indwelling catheter 180. The spine 150 is adapted to split the dressing film 40 into two separate portions upon removal of the spine 150. Specifically, when the spine 150 is pulled against the dressing film 40, the spine 150 cuts through the dressing film 40 therefore splitting the film 40 into two portions because the spine 150 is stronger than the dressing film 40. The spine can be a stronger plastic strip such as polyester. FIG. 10 shows how this embodiment can hold, or fixate/immobilize, the catheter hub onto a patient's skin during dressing change when the dressing film 40 is imparted with a spine 150 to break the dressing film 40 in half. With the spine 150, a health care professional can break the dressing film 40 and remove the primary portion 160 of the dressing film 40 first without dislodging the catheter hub, thus preventing the catheter to be pistoned out of place. When placing a new dressing on a patient, the insertion site can be covered first before the secondary portion 170 of the dressing film 40 (the old dressing) covering the catheter hub to be removed or pulled off, again, ensuring the security of the catheter. Since there is no adhesive between the catheter hub and the frame 140, the removal is easy.

Figure 11A:
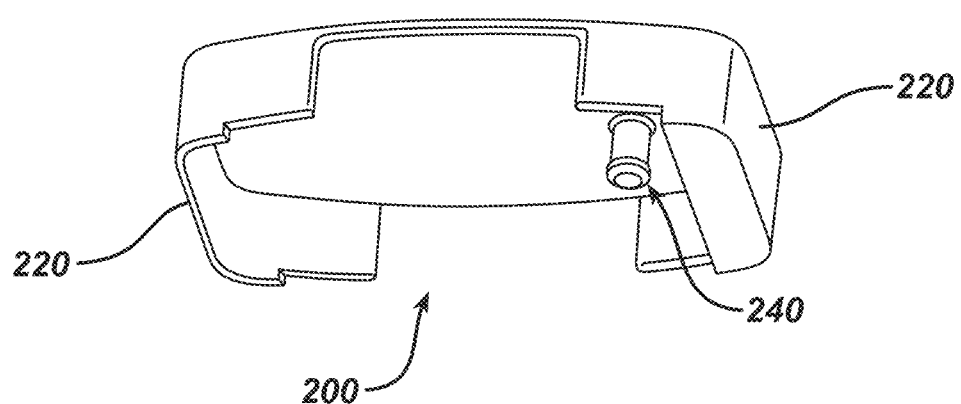
FIG. 11a illustrates an embodiment of a catheter fastener means, namely a cap that fully encapsulates a catheter hub.
Figure 11B:
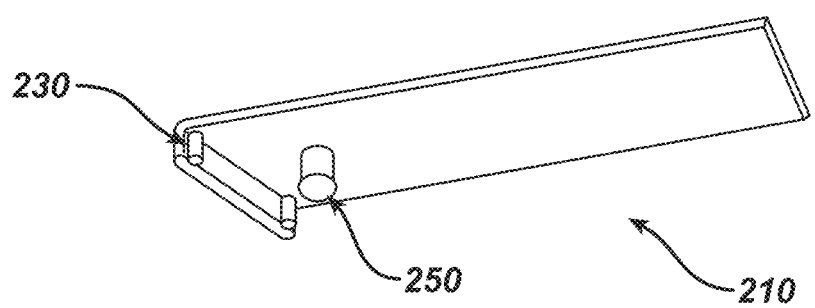
FIG. 11b illustrates another embodiment of a catheter fastener means, namely a cap that partially encapsulates a catheter hub.

Another embodiment for fixation of the catheter hub entails the use of a catheter fastener means, or a cap, as shown in FIGS. 11a and 11b. The caps 200 and 210 shown in FIGS. 11a and 11b are adapted to immobilize an indwelling catheter. In one embodiment, a cap 200 can fully cover or encapsulate a catheter hub as shown in FIG. 11a. In this embodiment, the cap 200 includes a wall or a border 220 on each side that is at least as high as the catheter hub. In another embodiment, a cap 210 can partially cover or encapsulate a catheter hub shown in FIG. 11b. In this embodiment, the cap 210 includes only one wall or border 230 on a single side. Each cap 200 and 210 includes a post 240 and 250 to loosely engage the catheter hub.

Figure 12:
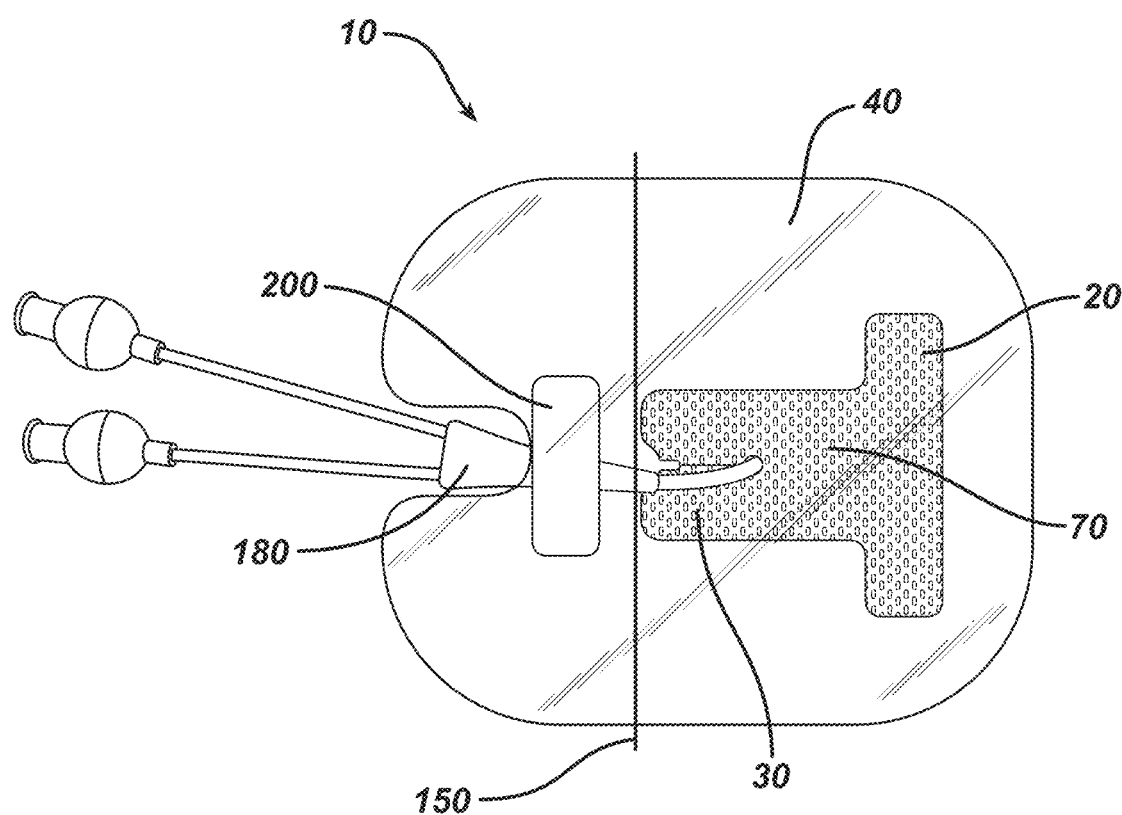
FIG. 12 illustrates a catheter fastener means in place on the skin of a patient.

Both cap 200 and 210 can be used in conjunction with a dressing device 10, and they come with the dressing device 10 packaged as a separate piece in a kit. The dressing film 40 with adhesive 80 is sized to cover the catheter fastener means to secure the fastener means to a patient's skin. The health care provider will place the cap 200 or 210 onto a catheter hub without having to worry about the adhesive. More specifically, the catheter fastener means of the invention does not have its own adhesive. Rather, the adhesive 80 on the proximal surface of the dressing film 40 sticks to the catheter fastener means that encapsulates the catheter hub. In this embodiment, the dressing film 40 will have a spine 150 as shown in FIG. 10. Since the cap 200/210 does not have adhesive, the removal during the dressing change is easy. FIG. 12 shows the cap 200/210 in place on the skin of a patient.

The pad 30, base 20, connector 70, and/or frame 140 of dressing device 10 may be formed from a pad impregnated with an antimicrobial agent. Furthermore the pad 30, base 20, connector 70, and frame 140 can be constructed with materials to address the need for fluid adsorption. These materials may have fluid absorption capacity of from 10 percent volume of fluid per volume of material to about 90 percent, such as absorbent foams to about 300 percent which corresponds to swellable gels or superabsorbents. In one embodiment, the material is absorbing 20-80 percent by volume of biological fluids or exudates. These elements may be at least translucent enough to see the catheter tubing through it. The elements may also be transparent for the purpose of visually assessing an insertion site of an indwelling catheter. In one embodiment, the range of transparency is from about 20 percent to about 100 percent transparent, such as 30 percent transparent.

The pad 30 is applied around indwelling catheter devices to prevent localized infection at the insertion site. The pad 30, base 20, connector 70, and frame 140 may comprise a mesh, foam, hydrogel, fabric, non-woven material, combinations thereof, or any material that provides the desired properties as described above.

Other suitable, but opaque, materials for the pad 30 include any tissue compatible absorbent foam, hydrogel, fabric, woven or non-woven material, cellulose-based material, or fiber structure or other suitable material. The absorbent material may comprise a felt, such as polyurethane foam; polyester mats; natural, synthetic, or hybrid synthetic/natural polyester; cellulose; alginate; polyacrylates; polyolefins; and cottons.

The antimicrobial agent that can be incorporated in the pad 30 can be an antimicrobial agent such as a chlorhexidine compound, for instance chlorhexidine gluconate or chlorhexidine acetate; silver compounds, for instance silver iodide, silver bromide, silver chloride, or nano-particulate metallic silver; benzalkonium chloride; polyhexamethylene biguanide (PHMB); triclosan; antibiotics such as metronidazole; alcohol; iodine; or other known antimicrobial compounds and combinations thereof that are compatible with skin and useful against a range of microorganisms, for example against known skin flora such as *Staphylococcus aureus* and methicillin-resistant *Staphylococcus aureus* (MRSA). In one embodiment, the antimicrobial agent is chlorhexidine gluconate, an agent known to be safe and effective and widely used as a surgical disinfectant. Plasticizers, colorants, surfactants, and stabilizers, singular or in combination, can also be incorporated in the pad 30.

Figure 13A:
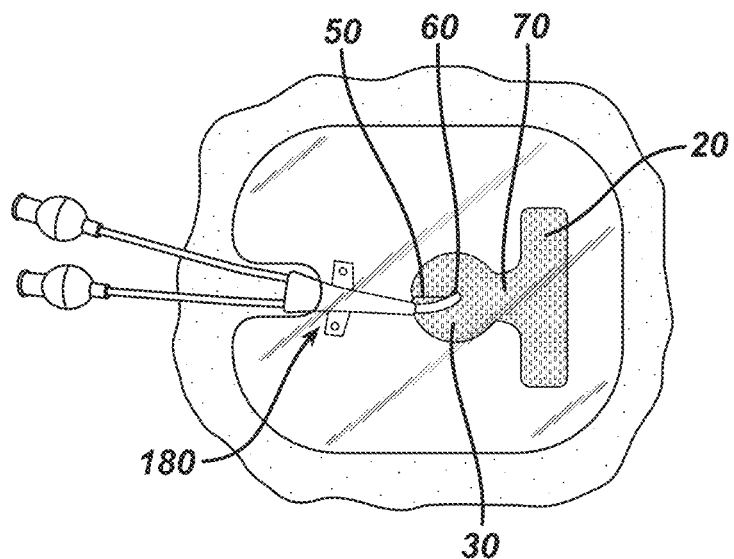
FIG. 13a illustrates the appearance of the design shown in 7a on the skin of a patient.
Figure 13B:
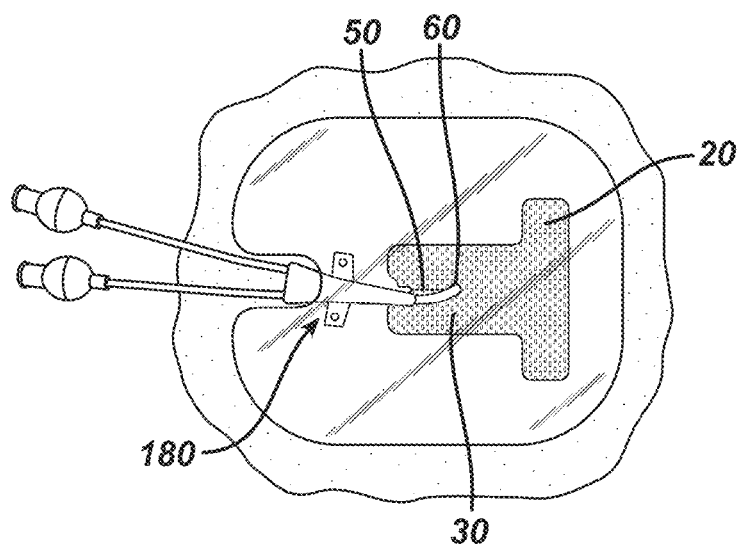
FIG. 13b illustrates the appearance of the design shown in 7b on the skin of a patient.
Figure 13C:
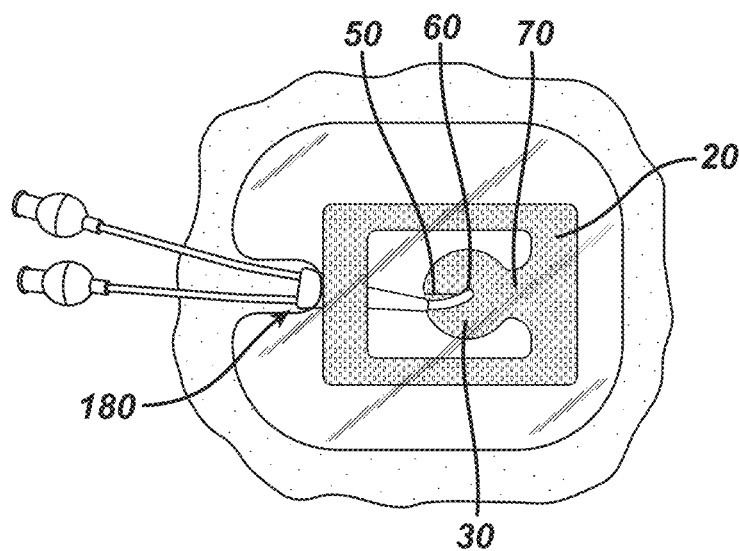
FIG. 13c illustrates the appearance of the design shown in 7c on the skin of a patient.

The pad 30, base 20, connector 70, and/or frame 140 of the dressing device 10 illustrated in the figures and disclosed herein may each not have any adhesive material and may be of any suitable shape as shown in FIGS. 7a through 7c. In one embodiment, the pad 30 of the dressing device 10 has a circular shape, as illustrated in FIGS. 7a and 7c. FIG. 7c further illustrates an embodiment of a dressing device 10 comprising a frame 140 connected to a base. FIGS. 13a, 13b, and 13c illustrate the appearance of the designs shown in FIGS. 7a, 7b, and 7c, respectively, on the skin of a patient. It is desired that there be complete 360 degree coverage around the insertion site of an indwelling catheter device, but the pad 30 may be any suitable shape.

The pad 30 of dressing device 10 is smaller than the film dressing 40. The diameter of the pad 30 may be varied as desired, depending upon the desired pharmaceutical dosage and duration of delivery. Ordinarily, a suitable pad diameter will be in a range of about 1 cm to about 10 cm, such as from 2 cm to about 5 cm, or about 2.5 cm. The diameter of the aperture 60 in the embodiments discussed above is selected so as to accommodate the appropriate catheter snugly, in tight engagement, with typical diameters ranging from 1 mm to about 20 mm, such as from 1 mm to 15 mm.

The thickness of the pad 30 may be varied as desired, depending upon the desired pharmaceutical dosage and duration of delivery. A suitable pad thickness will be in a range of about 0.3 mm to about 5 mm such as 1 mm to 3 mm.

The dressing device 10 described herein may be adapted for use with an indwelling catheter that has punctured the skin of a patient and has a portion of the catheter protruding from the skin by further comprising a slit as discussed above. Specifically, the pads 30 of the dressing devices 10 have slits 50 that can be formed by cutting, punching, or similar. The widths of slits 50 of the pads 30 are adapted to facilitate installation over the already installed indwelling catheter. The width of slits range from very small when the sides of the slit touch each other (i.e. a cut with a very narrow blade), corresponding to a slit from about less than 0.1 mm gap to about 1 mm gap, or from zero to about 50 microns gap. The slits 50 enable the dressing devices of the invention to fully surround the catheter at the insertion or puncture site. The size of the aperture 60 is adapted for fully surrounding the indwelling catheter protruding from the skin in a snug or loose configuration, with the diameter of the aperture ranging from about 90 percent of the outside diameter of the indwelling catheter to about 150 percent of the outside diameter of the indwelling catheter, such as 95 percent, 102 percent, 105 percent, or 110 percent of the outside diameter of the indwelling catheter. In one embodiment, the aperture diameter is equal to 100 percent of the outside diameter of the indwelling catheter.

The size of the base 20 can be from 1 inch to 3 inch. The size of the connector 70 can be from 0.2 diameters of pad 30 to 1 diameter of pad 30. In one embodiment, the connector 70 is 0.5 to 0.7 diameters of the pad 30. The frame 140 can be rectangular in shape and have a size of the sides from 1 inch to 5 inches. The base 20, connector 70, and frame 140 can be made from the same material as pad 30. The pad 30, connector 70, base 20, and frame 140 structure can be made by die-cutting or any other material cutting techniques, such as laser cutting. The size of this entire structure corresponds to the size of the frame which forms the outer boundary of the structure.

The dressing film 40 of dressing devices 10 can be formed from any adhesive translucent or transparent dressing for wounds, such as polyurethane film or copolyester film with thickness of about 50 to 350 microns, preferably 100-200 microns. Other suitable materials for the dressing film 40 include transparent polyester films with pressure sensitive biocompatible adhesive. The dressing film 40 has a layer of adhesive 80 disposed thereon, typically a pressure sensitive adhesive layer. The pressure-sensitive adhesive 80 can be any pressure sensitive adhesive known in the art. The adhesive 80 typically has a thickness from about 5-10 microns to about 50-200 microns. The adhesive can be continuous or discontinuous, i.e. applied in a patterned fashion. In one embodiment, the adhesive 80 is applied in stripes, thus providing for breathability of the dressing. In another embodiment, the adhesive 80 is not applied in the area that would encompass the frame opening 190 making removal of the dressing device 10 during dressing change easy.

In one embodiment, the dressing film 40 is at least partially translucent or transparent, with the light transmission from about 25 percent to about 100 percent, such as from 50 percent to about 99 percent) allowing a healthcare professional to visually check on the area of skin around the insertion site of indwelling catheter device. In yet another embodiment, the dressing film 40 is at least partially breathable meaning that air transmission is from about 500 cc/m$^2$/24 hours, to approximately 10,000 cc/m$^2$/24 hours or more and moisture vapor transmission rates (MVTR) of form about 1000 to 10000 g/m2/24 hours, depending on film thickness, film type.

The dressing film 40 of the dressing devices 10 described herein may be of any suitable shape. Suitable shapes of the dressing film 40 include, but are not limited to, round, square, rectangular, elliptical, trapezoidal, or any other suitable shape that ensures complete coverage beyond the outer perimeters of the base 20, the pad 30, the connector 70, and the frame 140, if present, and reliable adherence to skin.

The carrier or removable frame 130 can be a supporting sacrificial material that is supporting the dressing film 40 of the dressing device 10 prior to application and preventing wrinkling of the dressing film 40. In one process, known in the art, the removable frame 130 can be made by die-cutting and can be made of paper or similar materials. The paper can be used as a support during the dressing film 40 casting, with the dressing film 40 cast directly on the paper, resulting in attachment without any adhesive. Then the paper can be die-cut and part of the paper can be removed leaving the carrier frame.

The dressing devices 10 described herein may be of any suitable shape. In one embodiment, the dressing film 40 has a circular shape. Other suitable shapes include, but are not limited to rectangular, oval, trapezoidal, or any polygonal shape. One skilled in the art would understand how to modify the shape and size, including the length, width, and/or diameter, of the devices of the invention based on one's anticipated outcome, including but not limited to, intended use of the device and intended dosage and release profile of a antimicrobial agent(s).

Catheters for which the dressing devices of the present invention can be used are indwelling for some considerable time. Exemplary of indwelling catheters are central venous catheters, peripheral venous catheters, or any other indwelling catheters for delivery into and/or sampling from the patient. All of these indwelling catheters, when in place, have a portion of the catheter device that is external and left protruding from the skin, which can be the cause of infection around the insertion sites of the medical devices.

Figure 14A:
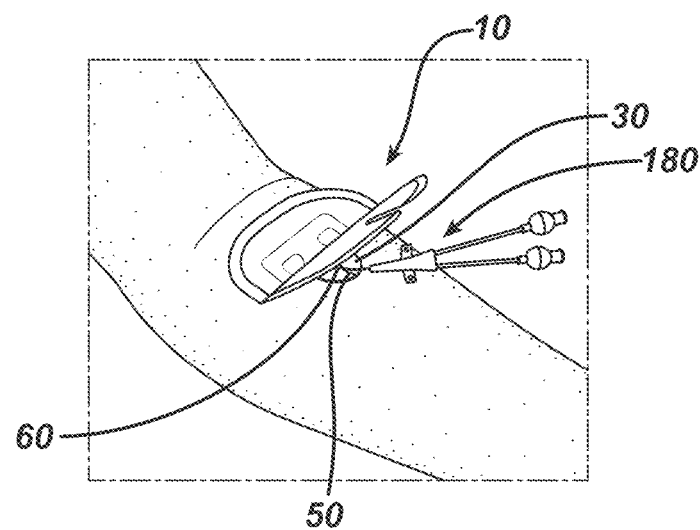
FIGS. 14a through 14f illustrate the steps involved in the deployment of a dressing device shown in FIGS. 9-11 (but without the spine), 7c, and 15c over an indwelling catheter.

The present invention also relates to a method of installing the dressing devices on a patient's skin over an indwelling catheter. FIGS. 14a through 14f illustrate various steps that may be involved in the deployment of a dressing device 10 shown in FIGS. 8a-b and 9a-b (but without the spine 150), over an indwelling catheter. As shown in FIG. 14a, when used over an indwelling catheter device, the dressing device 10 with a pad 30 is positioned in proximity to an indwelling catheter 180 insertion site opposite the tubing of the catheter. The catheter is inserted into the aperture 60 of the pad 30 through the slit 50. The indwelling catheter is guided through the slit 50, enabling the pad 30 to fully surround the catheter at the insertion or puncture site. The proximal surface of the pad 30 comprising an antimicrobial agent is thereby in contact with the skin surrounding the insertion or puncture site so that the dressing device 10 provides 360 degree or complete circumferential coverage around the catheter shaft.

Figure 14B:
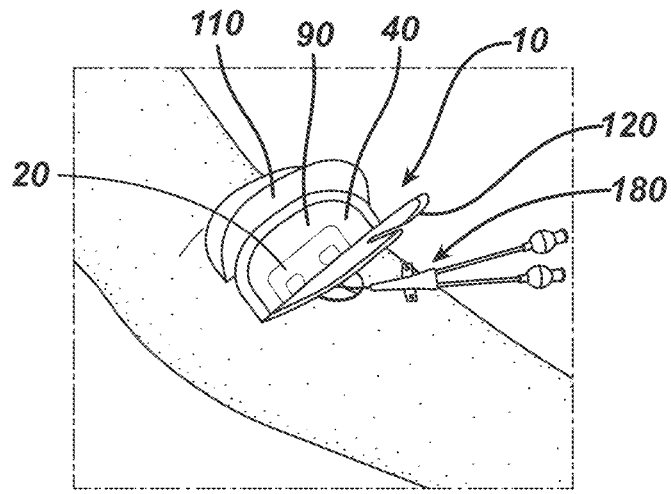
Figure 14C:
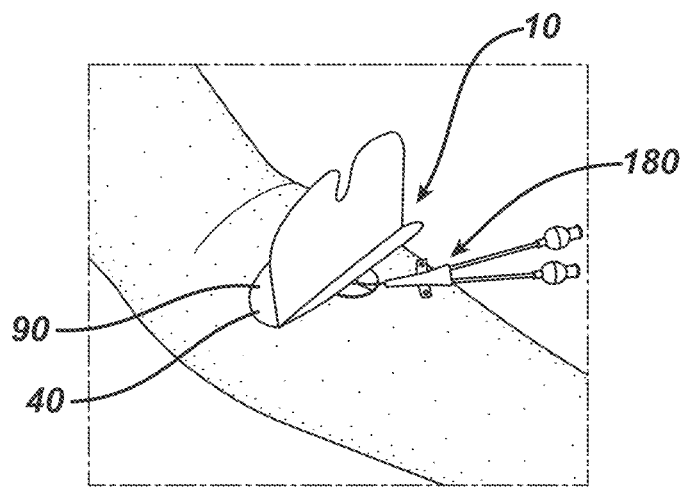

FIG. 14b illustrates the removal of the first release paper 110 attached to the proximal surfaces of the first portion 90 of the dressing film 40 and the base 20. FIG. 14c illustrates the next step of adhesively attaching the proximal surfaces of the first portion 90 of the dressing film 40 and the base 20 to the patient's skin.

Figure 14D:
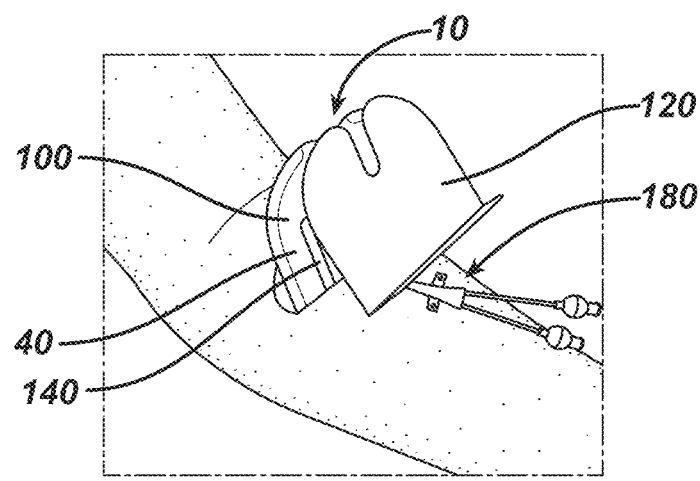
Figure 14E:
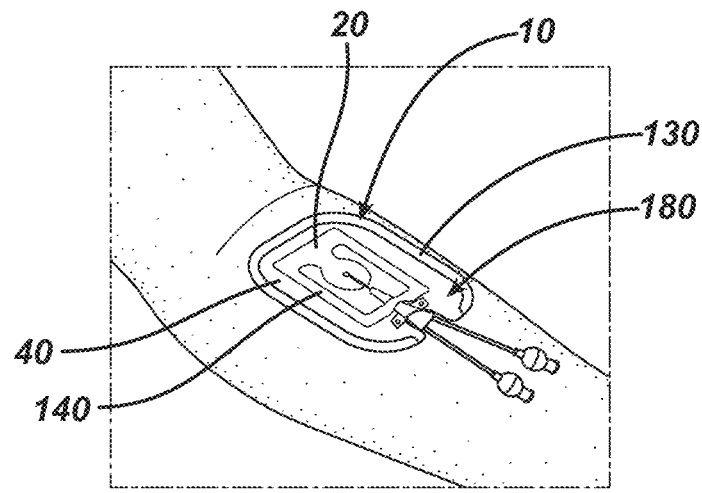
Figure 14F:
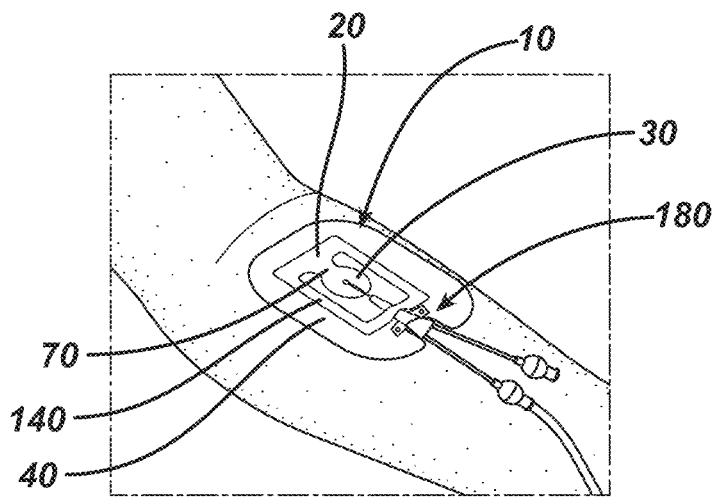

FIG. 14d illustrates the removal of the second release paper 120 attached to the proximal surfaces of the second portion 100 of the dressing film 40 and the frame 140. FIG. 14e illustrates the next step of unfolding and adhesively attaching the proximal surfaces of the second portion 100 of the dressing film 40 and the frame 140 to the patient's skin. FIG. 14e further illustrates the embodiment of a dressing device 10 further comprising a removable frame 130. FIG. 14f illustrates the dressing device 10 fully installed over an indwelling catheter 180 on a patient with the removable frame 130 removed from the distal surface of the dressing film 40.

If the dressing device 10 is purchased as a kit with a catheter fastener means, then the method of installing the dressing devices on a patient's skin over an indwelling catheter may comprise the additional step of immobilizing the indwelling catheter in a fixation means after the step unfolding and adhesively attaching the proximal surface of the second portion 100 of the dressing film 40 to the skin of a patient.

Figure 15A:
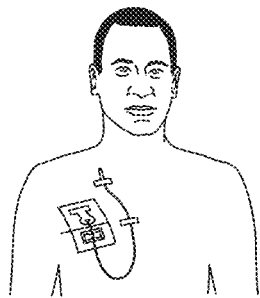
FIG. 15a illustrates the dressing device fully installed over an indwelling catheter on a patient with a central venous catheter (CVC).

The present invention also relates to a method of replacing dressing devices 10 on a patient's skin over an indwelling catheter 180, specifically when a spine 150 is embedded into the dressing film 40 as described herein. The dressing device 10 to be replaced is referred to hereinafter as a first dressing device as shown in FIG. 15a for the case of a central venous catheter, and the new dressing device (replacing the first dressing device) is referred to hereinafter as a second dressing device. Both the first and second dressing devices may comprise a spine 150 embedded into the dressing film 40, wherein the spine 150 divides the dressing film 40 into a primary portion 160 and a secondary portion 170, the primary portion 160 comprising a base 20, a connector 70, and a pad 30, the secondary portion 170 comprising a portion of the dressing film 40 that would cover at least a part of an indwelling catheter 180. The spine 150 of the first and second dressing devices are adapted to split the dressing films 40 of the first and second dressing devices into two separate portions upon removal of the spines 150 as shown in FIGS. 15b and 15c.

The first dressing device of this method is installed over an indwelling catheter 180 on the skin of a patient as described above. Specifically, the first dressing is positioned with the pad 30 in proximity to an insertion site of an indwelling catheter 180, and the catheter is inserted into the aperture 60 through the slit 50. The first release paper 110 is removed, and the proximal surface of the first portion 90 of the dressing film 40 is adhesively attached to the skin of a patient. The second release paper 120 is then removed, and the proximal surface of the second portion 100 of the dressing film is unfolded and adhesively attached to the patient's skin. The first dressing device is then used for a period of time ranging from 12 hours to 10 days, preferably 24 hours to 7 days.

Figure 15B:
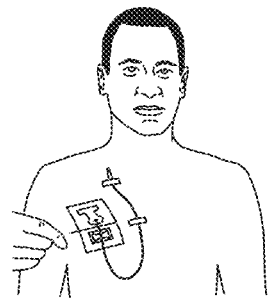
FIG. 15b illustrates the pulling of the spin to break the dressing device into two portions.
Figure 15C:
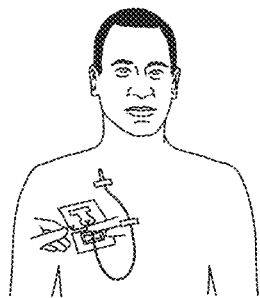
FIG. 15c illustrates the dressing device broken into two portions and the initial removal of the first portion containing the antimicrobial pad.
Figure 15D:
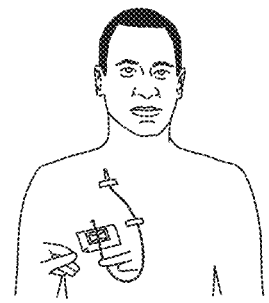
FIG. 15d illustrates the removal of the remaining second portion of the dressing device containing the fixation means.

When a user wishes to replace the first dressing device, the spine 150 embedded into the dressing film 40 of the first dressing device is pulled and removed as shown in FIG. 15b. The primary portion 160 of the dressing film 40, the base 20, the connector 70, and the pad 30 of the first dressing device, is then removed from the patient's skin as shown in FIGS. 15c and 15d. The healthcare professional may then remove the secondary portion 170 of the dressing film 40 of the first dressing device as shown in FIG. 15d.

Figure 15E:
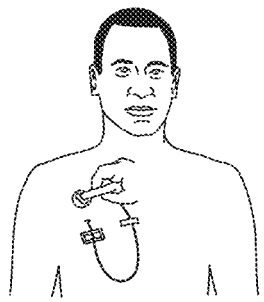
FIG. 15e illustrates the total removal of the first dressing and the cleaning of the insertion site in preparation for the application of the second dressing.

A healthcare professional may then clean the insertion site based on the hospital or CDC protocol as shown in FIG. 15e and then install the second dressing device per procedure described above. The tube of the indwelling catheter 180 is inserted into the aperture 60 through the slit 50 of the pad 30 of the second dressing device. The first release paper 110 of the second dressing is removed, and the proximal surface of the first portion 90 of the dressing film 40 of the second dressing device is adhesively attached to the patient's skin. The healthcare professional may then remove the second release paper 120 of the second dressing device and then unfold and adhesively attach the proximal surface of the second portion 100 of the dressing film 40 of the second dressing device to the skin of a patient.

The invention being thus described, it will be apparent that the same may be varied in many ways. Such variations are not to be regarded as a departure from the spirit and scope of the invention, and all such modifications as would be obvious to one skilled in the art are intended to be included within the scope of the following claims.

I claim:
1. A dressing device comprising:
 a base connected to a pad and to a dressing film, the base, the pad, and the dressing film each having a proximal surface facing a patient's skin and a distal surface facing away from the skin;

wherein the pad has a slit extending from a perimeter of the pad to an aperture proximate to a center of the pad and an antimicrobial agent;

wherein the base is connected to the pad by a connector bridging the base and the perimeter of the pad;

wherein a frame, having a proximal surface facing a patient's skin and a distal surface facing away from the skin, is connected to the base and comprises an opening that surrounds the pad and the connector;

wherein the base, pad, connector, and frame are formed from the same material;

wherein the dressing film comprises an adhesive disposed on the proximal surface of the dressing film and has a first portion and a second portion and the proximal surface of the first portion of the dressing film is adhesively attached to the distal surface of the base;

wherein the dressing film further comprises a first release paper attached to the proximal surfaces of the first portion of the dressing film and the base and a second release paper attached to the proximal surface of the second portion of the dressing film;

wherein the second portion of the dressing film is folded onto the first portion of the dressing film so that the distal surface of the first portion of the dressing film is in proximity to the distal surface of the second portion of the dressing film; and wherein a spine is embedded into the dressing film, the spine dividing the dressing film into a primary portion and a secondary portion, the primary portion comprising the base, the connector, and the pad, the secondary portion comprising a portion of the dressing film that would cover at least a part of the frame and a part of an indwelling catheter, the spine adapted to split the dressing film into two separate portions upon removal of the spine.

2. The dressing of claim 1, wherein the second portion of the dressing film has no adhesive in an area proximate to the distal surface of the pad.

3. The dressing of claim 1, wherein the dressing film has a removable frame attached to a peripheral area of the distal surface of the dressing film.

4. The dressing of claim 1, wherein the dressing film is at least partially transparent.

5. The dressing of claim 1, wherein the dressing film is at least partially breathable.

6. The dressing of claim 1, wherein the frame and the base and the connector also comprise the antimicrobial agent.

7. The dressing of claim 1, wherein the second portion of the dressing film is proximate to and has a size adapted to cover the connector, pad, and frame.

8. The dressing of claim 1, wherein the first portion of the dressing film has a size adapted to cover the base.

9. The dressing of claim 1, wherein the pad has fluid absorption capacity.

10. The dressing of claim 1, wherein the pad comprises a mesh, foam, hydrogel, fabric, non-woven material, or combinations thereof.

11. The dressing of claim 1, wherein the base comprises an adhesive disposed on the proximal surface of the base.

12. The dressing of claim 1, wherein the base also comprises the antimicrobial agent.

13. A kit comprising the dressing of claim 1 and further comprising a catheter fastener means, wherein the catheter fastener means is adapted to immobilize an indwelling catheter, and wherein the dressing film is sized to cover the fastener means and to attach the fastener means to a patient's skin.

14. The kit of claim 13 wherein the fastener means is a cap.

15. A method of replacing the dressing of claim 1, comprising the steps of:
providing a first dressing according to claim 1 and:
using a sterile technique to disinfect the skin around a catheter insertion site and allow it to dry completely;
positioning the first dressing with the pad in proximity to an insertion site of an indwelling catheter and inserting the catheter into the aperture through the slit;
removing the first release paper;
adhesively attaching the proximal surface of the first portion of the dressing film to the skin;
removing the second release paper;
unfolding and adhesively attaching the proximal surface of the second portion of the dressing film to the skin;
using the first dressing for a period of time;
pulling on the spine and removing the spine;
removing from a patient's skin the primary portion of the dressing film and the base and the pad;
removing the secondary portion of the dressing film of the first dressing;
using the sterile technique and disinfect the skin around the catheter insertion site and allow it to dry completely;
providing a second dressing according to claim 1 and:
inserting the catheter into the aperture through the slit of the pad of the second dressing;
removing the first release paper of the second dressing;
adhesively attaching the proximal surface of the first portion of the dressing film of the second dressing to the skin;
removing the second release paper of the second dressing;
unfolding and adhesively attaching the proximal surface of the second portion of the dressing film of the second dressing to the skin.

16. A method of making of the dressing of claim 1, comprising:
providing a base connected to a pad by a connector bridging the base and the perimeter of the pad, wherein a frame is connected to the base and comprises an opening that surrounds the pad and the connector, wherein the pad has a slit extending from a perimeter of the pad to an aperture proximate to a center of the pad and an antimicrobial agent, the base, frame, and the pad each having a proximal surface facing a patient's skin and a distal surface facing away from the skin;
providing a dressing film with a proximal surface facing the skin and a distal surface facing away from the skin and comprising an adhesive disposed on the proximal surface of the dressing film and having a first portion and a second portion, wherein a spine is embedded into the dressing film, the spine dividing the dressing film into a primary portion and a secondary portion, the primary portion comprising the base, the connector, the pad and part of the frame, the secondary portion comprising a portion of the dressing film that would cover part of the frame and at least a part of an indwelling catheter, the spine adapted to split the dressing film into two separate portions upon removal of the spine;
adhesively attaching the proximal surface of the dressing film to the distal surface of the base and the frame;
attaching first and second release papers to the proximal surfaces of first and second portions of the dressing film, respectively, and;

folding the second portion of the dressing film onto the first portion of the dressing film so that the distal surface of the first portion of the dressing film is in proximity to the distal surface of the second portion of the dressing film.

* * * * *